United States Patent
Wurster et al.

(10) Patent No.: US 6,521,632 B2
(45) Date of Patent: Feb. 18, 2003

(54) METHOD FOR THE TREATMENT OR PREVENTION OF A DISEASE MEDIATED BY THE ALPHA-2B-ADRENOCEPTOR

(75) Inventors: Siegfried Wurster, Piikkiö (FI); Mia Engström, Turku (FI); Liisa Huovinen, Littoinen (FI); Sari Kalliokoski, Turku (FI); Leila Kelanne, Piispanristi (FI); Eeva-Liisa Savola, Turku (FI)

(73) Assignee: Oy Juvantia Pharma LTD, Turku (FI)

( * ) Notice: Subject to any disclaimer, the term of this patent is extended or adjusted under 35 U.S.C. 154(b) by 107 days.

(21) Appl. No.: 09/773,512

(22) Filed: Feb. 2, 2001

(65) Prior Publication Data

US 2002/0058618 A1 May 16, 2002

Related U.S. Application Data

(60) Provisional application No. 60/182,021, filed on Feb. 11, 2000.

(51) Int. Cl.[7] ............... A61K 31/505; A61K 31/506; C07D 239/69
(52) U.S. Cl. .................... 514/275; 544/297
(58) Field of Search .................... 514/275; 544/297

(56) References Cited

U.S. PATENT DOCUMENTS

| 4,604,398 A | 8/1986 | Ward | 514/294 |
| 5,292,740 A | 3/1994 | Burri et al. | 514/256 |
| 5,530,118 A * | 6/1996 | Oinuma et al. | 540/364 |

OTHER PUBLICATIONS

*Fujikura et al., "Studies on Benzenesulfonamide Derivatives With .alpha.–and .beta.–adrenergic Antagonistic and Antihypertensive Activities." 98 *STN Int'l* 178855 (1982).

Michel et al., "Assessment of Imiloxan as a Selective $\alpha_{2B}$–adrenoceptor Antagonist," 99 *Br. J. Pharmacol.* 560 (1990).

Link et al., "Cardiovascular Regulation in Mice Lacking $\alpha_2$–adrenergic Receptor Subtypes b and c," 273 *Science* 803 (1996).

MacDonald et al., "Gene Targeting—Homing in on $\alpha_2$–Adrenoceptor–subtype Function," 18 *Trends Pharmacol Sci* 211 (1997).

* cited by examiner

*Primary Examiner*—Jeffrey E. Russel
(74) *Attorney, Agent, or Firm*—James C. Lydon

(57) ABSTRACT

A method for the treatment or prevention of a disease mediated by the alpha-2B-adrenoceptor in a mammal. The method includes administering to the mammal an effective amount of a selective (alpha-2B-adrenoceptor antagonist, where the antagonist is a compound selected from the group consisting of compounds A, B, C, D and E disclosed in Scheme I, or a pharmaceutically acceptable salt of the compound.

8 Claims, No Drawings

METHOD FOR THE TREATMENT OR PREVENTION OF A DISEASE MEDIATED BY THE ALPHA-2B-ADRENOCEPTOR

This application claims priority of U.S. provisional application Ser. No. 60/182,021, filed Feb. 11, 2000.

The present invention relates to a method for the treatment or prevention of diseases mediated by the alpha-2B-adrenoceptor in mammals, by administering to said mammal a selective alpha-2B-adrenoceptor antagonist.

BACKGROUND OF THE INVENTION

The publications and other materials used herein to illuminate the background of the invention, and in particular, cases to provide additional details respecting the practice, are incorporated by reference.

The selective alpha-2B-adrenoceptor antagonists shown in Scheme I below are all previously known. The inventors obtained the compounds A (ordering No AE-848/34956037), C (ordering No AF-399/36012031) and D (ordering No AH-034/34347043) from SPECS and BioSPECS B.V., Fleminglaan 16, 2289 C P Rijswijk, The Netherlands. The compounds B (ordering No 653716) and E (ordering No 569063) were supplied by ChemBridge Corporation, 16981 Via Tazon, Suite G, San Diego Calif. 92127.

It is known that alpha-2B-adrenoceptors mediate vascular contractions. Therefore, alpha-2B-antagonists are useful in the treatment or prevention of diseases involving vascular contraction. It has also been found that there is a genetic polymorphism in the alpha-2B-adrenoceptor gene at certain individuals. It has been observed that the alpha-2B-adrenoceptor protein at some subjects has a deletion of 3 glutamates from the glutamic acid repeat element of 12 glutamates (amino acids 297–309), in an acid trech of 17 amino acids, located in the third intracellular loop of the receptor polypeptide (Heinonen et al., 1999).

OBJECTS AND SUMMARY OF THE INVENTION

It has now been found that the compounds selected from the group consisting of compound A, B, C, D and E, the formulae of which are disclosed in Scheme I, are selective alpha-2B-adrenoceptor antagonists.

Thus, this invention relates to a method for the treatment or prevention of a disease mediated by the alpba-2B-adrenoceptor in a mammal, said method comprising administering to said mammal an effective amount of a selective alpha-2B-adrenoceptor antagonist, wherein said antagonist is a compotmd selected from the group consisting of compound A, B, C, D and E disclosed in Scheme 1, or a pharmaceutically acceptable salt of said compound.

DETAILED DESCRIPTION OF THE INVENTION

Alpha-2B-adrenoceptor antagonists are useful in the treatment and/or prevention of many diseases.

Individuals having a deletion in the alpha-2B-adrenocepter protein (Heinonen et al., 1999), particularly the deletion/deletion genotype (D/D genotype) is an important target group which benefits from administration of selective alpha-2B-adrenoceptor antagonists.

It has been found that in a population-based cohort of Finnish middle-aged men that subjects with a D/D genotype of the alpha-2B-adrenoceptor gene have a significantly elevated risk for acute myocardial infarction (AMI) in a five-year follow-up study. The risk for AMI was increased in subjects who had no previously diagnosed coronary heart disease (CHD) at the study outset. Therefore, it has been postulated that the D/D genotype is related to an impaired capacity to down-regulate alpha-2B-adrenoceptor function during sustained receptor activation. Therefore, alpha-2B-adrenoceptors are believed to be involved in the pathogenesis of a significant fraction of all cases of AMI, especially in subjects with the D/D genotype, but also in I/D and I/I subjects (I means "insertion" and stands for the "normal" allele).

The alpha-2B-adrenoceptor antagonists as disclosed in this invention would be particulaly useful in the treatment or prevention of coronary heart diseases. As examples can be mentioned.

a) Acute AMI

If alpha-2B-adrenoceptor dependent vasoconstriction is a causative factor in some cases of AMI, then antagonism of these receptors should restore coronary circulation and reduce the ischemic myocardial damage.

b) Unstable Angina Pectolis

An alpha-2B-adrenoceptor antagonist will relieve the vasoconstrictive component in the sustained ischemic episode, thus alleviating the symptoms and preventing AMI.

c) Prinzietal's Variant Form of Angina Pectoris

Vasoconstriction is a key factor in the pathogenesis of Prinzmetal's angina, and an alpha-2B-adrenoceptor antagonist may resolve and prevent attacks.

d) Other Forms of Chronic Angina Pectoris and CHD

An alpha-2B-adrenoceptor antagonist will help to alleviate the vasoconstrictive component in all types of CHD, providing both symptomatic relief and protection from AMI. A general reduction in vascular tone will contribute to this by reducing venous return, cardiac workload and oxygen consumption (a nitrate-type effect; see below).

e) Prevention of Restenosis After Coroary Angioplasty in Cases where Vasoconstriction Plays a Role in Restenosis Furhennore, the alpha-2B-adrenoceptor antagonists as disclosed in this invention would be useful in the treatment or prevention of essential hypertension, especially in subjects with increased sympathetic activity and a hyperdynamic circulatory system.

In the study mentioned above, the D/D variant of the alpha-2B-adrenoceptor gene was not clearly associated with blood pressure. The inventors believe that this was due to two main factors, 1) antihypertensive treatment, and 2) complex regulation of systemic blood pressure. In another study (Heinonen et al.), it was observed that the D/D genotype was associated with reduced basal metabolic rate and reduced heart rate. These associations probably reflect increased vascular resistance in these subjects.

In transgenic mice with targeted inactivation of the alpha-2B-adrenoceptor gene, intravenously administered alpha-2-adrenoceptor agollists fail to induce the characteristic blood pressure elevation which is seen in normal animals and also in humans after large doses of such drugs (Link et al., 1996). The hypotensive effect of these drugs was markedly accentuated. This demonstrates that alpha-2B-adrenoceptors mediate vascular contraction. Thus, an antagonist should reduce blood pressure. This effect has not been seen with alpha-2B-nonselective alpha-2-adrenoceptor antagonists, because antagonism of alpha-2A-adrenoceptors increases sympathetic outflow, cardiac output and blood pressure. In mice with dysfunctional alpha-2A-adrenioceptors, alpha-2-adreoceptor agonists caused an accentuated hypertensive response and no hypotension (MacMillan et al., 1996).

An alpha-2B-adrenoceptor antagonist is postulated to have favourable effects in hypertensive subjects through their effects on renal function, muscle blood flow, and also on vascular resistance in other vascular beds. The anti-AMI effect of such a drug will be an additional benefit, as hypertension is a significant risk factor for AMI. This protection is due to thuee factors: 1) a reduction in systemic blood pressure, 2) decreased risk of coronary vasoconstiction, and 3) a nitrate-like effect on venous return, myocardial workload and oxygen consumption.

Moreover, the alpha-2B-adrenoceptor antagonists as disclosed in this invention would be useful in the treatment or prevention of other vascular diseases. Specifically, benefits can be expected in the treatment or prevention of

- vasoconstriction and hypoxic brain damage subsequent to subarachnoid haemorrhage,
- migraine,
- Raynaud's disease and cold intolerance,
- pre-eclampsia,
- male erectile dysfunction, and
- obesity and the metabolic syndrome.

The last mentioned effect is due to the fact that reduced muscle blood flow and reduced basal metabolic rate contribute to the development of obesity and hypertension. An alpha-2B-adrenoceptor antagonist will, by increasing the muscle blood flow, increase energy expenditure and shift the caloric balance to a favourable direction.

The alpha-2B-adrenoceptor antagonists disclosed in this invention are also useful in anesthesia and analgesia to potentiate the clinical efficacy of alpha-2-adrenoceptor agonists which are not selective for the alpha-2B-adrenoceptor subtype. By blocking the vasoconstiiction induced by these agonists, a simultaneously administered alpha-2B-adrenoceptor antagonist will allow the use of larger doses of said agonists, up to anesthetic dose levels which have not previously been possible in man, only in veteinary anesthetic practice.

EXPERIMENTAL SECTION

Binding Affinity Human Alpha-2-adrenoceptor

The affinity of test compounds for the three human $\alpha_2$-adrenoceptor subtypes ($\alpha_{2A}$, $\alpha_{2B}$ and $\alpha_{2C}$) was determined in competition binding assays with $^3$H-rauwolscine. The biological material for these experiments consisted of membranes from Shionogi S115 cells stably transfected with either of the three human $\alpha_2$ subtypes (Marjarnaki et al. 1992). Membrane (5–10 μg of total protein per sample) and 1 nM–2 nM $^3$H-rauwolscine (specific activity 78 Ci/mrnmol) were incubated in 50 mM $KH_2PO_4$, pH 7.5 with 6 concentrations of the compounds. Each concentration was run in duplicate. Nonspecific binding was defined by 100 μM oxymetazoline and corresponded to 5–15% of total binding. After 30 mim at room temperature, incubations were terminated by rapid vacuum filtration through GF/B glass fiber filter and three 5 ml washes with icecold incubation buffer. The filters were then dried, impregnated with scintillate and their radioactivity was measured by scintillation counting. The analysis of the experiments was carried out by nonlineair least square curve fitting. Experimentally determined IC50 values were converted to Ki's by making use of the Cheng-Prusoff equation (Cheng and Prusoff, 1973). Experiments were repeated a minimum of three times.

TABLE 1

Binding affinities on human $\alpha_2$-adrenoceptor subtypes
Data is presented as Ki's in nM (Mean ± SEM),
n = 3 unless indicated otherwise

| Compound | alpha-2A | alpha-2B | alpha-2C |
|---|---|---|---|
| A | 4100 ± 200 | 30 ± 4 | >4700 |
| C | >30000 (n = 2) | 1860 (n = 2) | >30000 (n = 2) |
| D | >30000 | 530 ± 90 | >30000 |
| B | >30000 | 215 ± 60 | >30000 |
| E | >100000 | 2900 ± 300 | >100000 |

Binding Affinity Rat Cortical $\alpha_1$-adrenoceptor

The affinity for rat neocortical $\alpha_1$-adrenoceptors was determined in competition binding assays with $^3$H-prazosin. The biological material for these assays consisted of membranes from rat neocortex. Membrane suspensions (100–200 μg of total protein per sample) and 0.2 nM–0.25 nM of $^3$H-prazosin (specific activity 74 Ci/mmol) were incubated with 6 concentrations of compounds in a total volume of 0.25 ml (50 mM Tris pH 7.7 at 25° C). Each concentration was run in duplicate. Nonspecific binding was defined by 10 μM phentolamine methanesulfonate and corresponded to 25–30% of total binding. After 30 min at room temperature, incubations was terminated by rapid filtration through GF/B glass-fiber filter mats and three washes with ice-cold 10 mM Tris (pH 7.7 at 4° C.). After drying, a solid scintillate was melted onto the filter mats, and their radioactivity was measured by scintillation counting.

Result

At concentrations of up to 30 μM, compound A caused insufficient displacement of $^3$H-prazosin to allow the estimate of an $IC_{50}$ value. It is therefore concluded that the $IC_{50}$ and the Ki of compound A must be >30000 nM.

Antagonist Activity on Human $a_2$-adrenoceptor Subtypes

Antagonist potencies were determined as the ability of test compounds to competitively inhibit epinephrine-stimulated $^{35}$S-GTPγS binding to G proteins (Tian et al., 1993; Wieland and Jalcobs, 1994; Jasper et al., 1998) in membranes of CHO cells stably transfected with one of the three human $\alpha_2$ subtypes (Pohjanoksa et al., 1997; Marjam äki et al., 1998). Membranes (2–6 μg of protein per samnple) and 12 concentrations of test compound were preincubated for 30 min with a fixed concentration fo epinephrine (5 μM for $\alpha_{2A}$, 15 μM for $\alpha_{2B}$, 5 μM for $\alpha_2$C) in 50 mM Tris, 5 mM $MgCl_2$, 150 mM NaCl, 1 mM DTT, 1 mM EDTA, 10 μuM GDP, 30 μM ascoerbic acid, pH 7.4 at room temperature. Binding of radiolabel was started by the addition of trace amounts of $^{35}$S-GTPγS (0.08 nM–0.15 nM, specific activity 1250 Ci/mmol) to the incubation mixture. After an additional 60 min at room temperature, the incubation was terminated by rapid vacuum filtration through glass fiber filter. Filters were washed three times with 5 ml icecold wash buffer (20 mM Tris, 5 mM $MgCl_2$, 1 mM EDTA pH 7.4 at room temperature), dried and counted for radioactivity in a scintiallation counter. Analysis of experiments was carried out by nonlinear least square fitting. Experiments were repeated at least three times.

TABLE 2

Antagonist effect of compound A and compound B on the human $\alpha_2$-adrenoceptor subtypes
Data is presented as KB's in nM (Mean ± SEM), n is a minimum of three experiments.

| Compound | alpha-2A* | alpha-2B | alpha-2C* |
|---|---|---|---|
| A | 2400 ± 700 | 73 ± 23 | 2400 ± 900 |
| B | >10000 | 250 ± 80 | >10000 |

*only incomplete dose-response curves could be obtained, KB numbers are minimum estimates For the purpose of the invention, the alpha-2B-adrenoceptor antagonist as disclosed in Scheme I or its pharmaceutically acceptable salt can be administered by various routes. The suitable administration forms include, for example, oral formulations; parenteral injections including intravenous, intramuscular, intradermal and subcutanous injections; transdermal or rectal administration forms. The required dosage of the compounds of the alpha-2B-adrenoceptor antagonist will vary with the particular condition being treated, the severity of the condition, the duration of the treatment, the administration route and the specific compound being employed. The suitable dose varies in the range 5 μg to 100 mg per kg body weight and day for an adult person.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

Scheme I

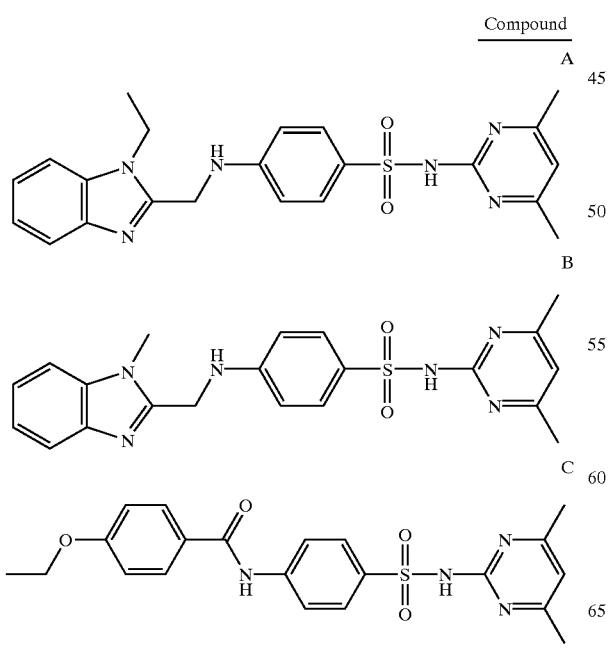
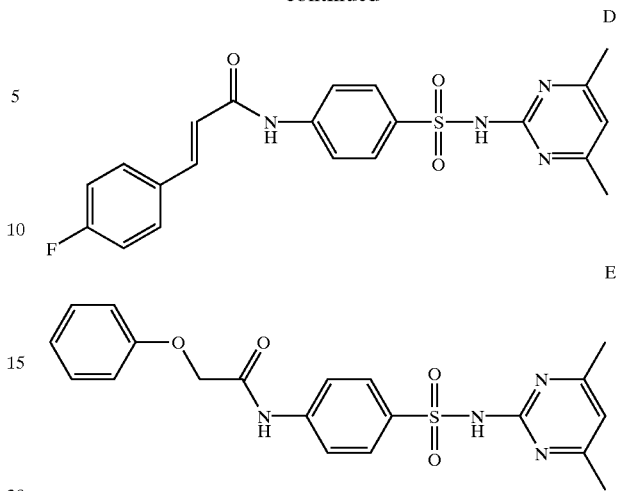

REFERENCES

Cheng, Y., and Prusoff, W. H., 1973. Biochem. Pharmacol. 22: 3099

Jasper, J. R., Lesnick, J. D., Chang, L. K., Yamanashi, S. S., Chang, T. C., Hsu, S. A. O., Daunt, D. A., Bonhaus, D. W., and Egen, R. M., 1998. Biochem. Pharmacol. 55:1035

Marjamäki, A., Ala-Uotila, S., Luomala, K., Perädlä, M., Jansson, C., Jalkanen, M., Regan, J. W., and Scheinin, M., 1992. Biochem. Biophys. Acta 1134: 169

Marjamäki, A., Pihlavisto, M., Cockcroft, V., Heinonen, P., Savola, J.-M., and Scheinin, M., 1998. Mol. Phannacol. 53: 370

Pohjanoksa, K., Jansson, C. C., Luomala, K., Marjamäki, A., Savola, J.-M., and Scheinin, M., 1997. Eur. J. Pharmacol. 35: 53

Tian, W.-N., Duzic, E., Lanier, S. M., and Deth, R. C., 1993. Mol. Pharmacol. 45: 524

Wieland, T., and Jakobs, K. H., 1994. Meth. Enzymol. 237: 3

Heinonen et al. 1999, The Journal of Clinical Endocrinology & Metabolism, 84:2429

Link R E et al., 1996, Science 273:803

Macmillan L B et al., 1996, Science 273:801

What is claimed is:

1. A method for the treatment or prevention of a disease mediated by the alpha-2B-adrenoceptor in a mammal, said method comprising administering to said mammal an effective amount of a selective alpha-2B-adrenoceptor antagonist, wherein said antagonist is a compound selected from the group consisting of compounds A, B, C and E, or a pharmaceutically acceptable salt of said compound, wherein said compounds A, B, C and E have the following structures:

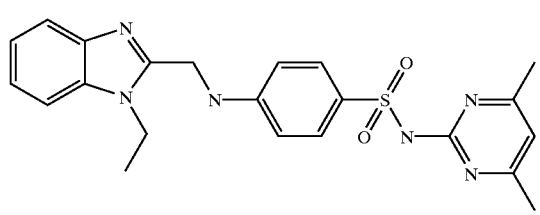

-continued

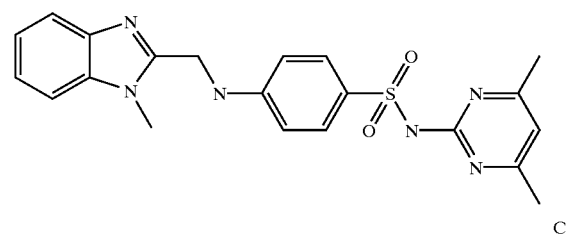

B

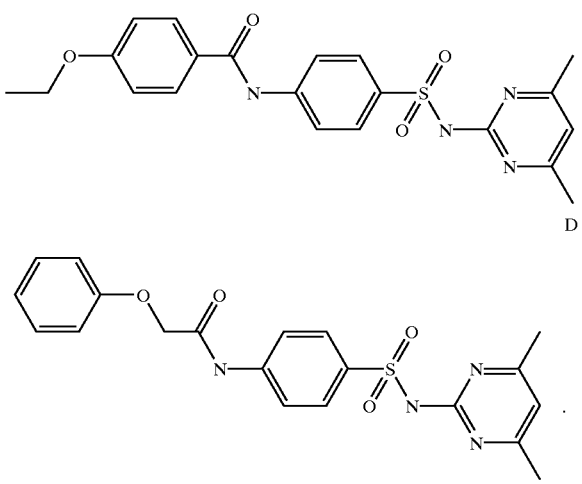

C

D

2. The method according to claim 1, wherein the disease is a coronary heart disease (CHD).

3. The method according to claim 2, wherein the disease is
   acute myocardial infarction (AMI),
   unstable angina pectoris,
   Prinzmetal's variant form of angina pectouis,
   other forms of chronic angina pectotis and CHD, or
   restenosis after coroniary angioplasty.

4. The method according to claim 1, wherein the disease is essential hypertension.

5. The method according to claim 1, wherein the disease is a vascular disesase, which is
   vasoconstriction or hypoxic brain damage subsequent to subarachloid haemorrhage,
   migraine,
   Raynaud's disease or cold intolerance,
   pre-eclampsia,
   male erectile dysfunction, or
   obesity.

6. The method according to claim 1, wherein said alpha-2B-adrenoceptor antagonist is administered to a mammal to potentiate the clinical efficacy of an anesthetic and/or analgetic alpha-2-adrenoceptor agonist, said agonist not being selective for the alpha-2B-adrenoceptor subtype.

7. The method according to claim 1, wherein said alpha-2B-adrenoceptor antagonist is administered to an individual having a deletion of 3 glutamates from the glutanic acid repeat element of 12 glutamates (amino acids 297–309), in an acid strech of 17 amino acids, located in the third intracellular loop of the receptor polypeptide.

8. The method according to claim 7 wherein said individual is a deletion/deletion genotype.

* * * * *

UNITED STATES PATENT AND TRADEMARK OFFICE
CERTIFICATE OF CORRECTION

PATENT NO. : 6,521,632 B2
DATED : February 18, 2003
INVENTOR(S) : Wurster et al.

It is certified that error appears in the above-identified patent and that said Letters Patent is hereby corrected as shown below:

<u>Title page,</u>
Item [57], ABSTRACT,
Line 4, change "(alpha" to -- alpha --.

<u>Column 2,</u>
Line 20, change "Pectolis" to -- Pectoris --; and

<u>Column 4,</u>
Line 55, delete line spacing between text;

<u>Column 7,</u>
Line 20, change "D" to -- E --; and

<u>Column 8,</u>
Line 5, change "pectouis" to -- pectoris --.

Signed and Sealed this

Nineteenth Day of August, 2003

JAMES E. ROGAN
*Director of the United States Patent and Trademark Office*